(12) United States Patent
Vihko

(10) Patent No.: US 6,303,361 B1
(45) Date of Patent: Oct. 16, 2001

(54) HUMAN GLANDULAR KALLIKREIN-1 (HK2)

(75) Inventor: Pirkko Vihko, Helsinki (FI)

(73) Assignee: Orion-Yhtymä Oyj, Espoo (FI)

( * ) Notice: Subject to any disclaimer, the term of this patent is extended or adjusted under 35 U.S.C. 154(b) by 0 days.

(21) Appl. No.: 08/983,075

(22) PCT Filed: Jun. 28, 1996

(86) PCT No.: PCT/FI96/00382

§ 371 Date: Jun. 8, 1998

§ 102(e) Date: Jun. 8, 1998

(87) PCT Pub. No.: WO97/01630

PCT Pub. Date: Jan. 16, 1997

(30) Foreign Application Priority Data

Jun. 29, 1995 (GB) .................................................. 9513281

(51) Int. Cl.[7] .......................... G01N 33/53; C12P 21/06; C12N 15/00; C12N 9/50
(52) U.S. Cl. .......................... 435/226; 435/7.4; 435/7.92; 435/7.93; 435/69.1; 435/252.3; 435/320.1; 435/219; 435/6
(58) Field of Search ...................................... 435/219, 226, 435/7.4, 7.6, 7.92, 7.93, 240.26; 530/387.1, 388.26, 388.1; 436/547, 64, 813, 548

(56) References Cited

FOREIGN PATENT DOCUMENTS

WO 95/03334    2/1995   (WO) .
WO 95/30758   11/1995   (WO) .

OTHER PUBLICATIONS

Saedi MS et al. Overexpression of a human prostrate–specific glandular kallikrein, hK2, in *E.coli* and generation of antibodies. Molecular and Cellular Endocrinology 109:237–241, 1995.*

Lynette J. Schedlich et al., "Primary Structure of a Human Glandular Kallikrein Gene", Mary Ann Liebert, Inc., Publishers, DNA, vol. 6, No. 5, pp. 429–437 (1987).

Mauno Vihinen, "Modelling of prostate specific antigen and human glandular kallikrein structures", Biochem. Biophys. Res. Commun., vol. 204, p. 1251 (1994).

* cited by examiner

*Primary Examiner*—Rebecca E. Prouty
*Assistant Examiner*—Manjunath N. Rao
(74) *Attorney, Agent, or Firm*—Crowell & Moring LLP

(57) ABSTRACT

A new form of human glandular kallikrein-1 (hK2) found from cloning a prepro-hK2 cDNA from a human protrate cancer tissue cDNA library. The new form differs in sequence from the prior art form in that Arg[226] is substituted by Trp. A baculovirus expression vector is described for obtaining hK2 proteins, including Arg[226]-hK2 as an active mature protein directly from a culture medium.

18 Claims, 2 Drawing Sheets

SEQUENCE LISTING

<160> NUMBER OF SEQ ID NOS: 14

<210> SEQ ID NO 1
<211> LENGTH: 37
<212> TYPE: DNA
<213> ORGANISM: Homo sapiens

<400> SEQUENCE: 1
tcccccggga gatctcacca tgtgggacct ggttctc                                37

<210> SEQ ID NO 2
<211> LENGTH: 30
<212> TYPE: DNA
<213> ORGANISM: Homo sapiens

<400> SEQUENCE: 2
cgctctagat cagggttgg ctgcgatggt                                         30

<210> SEQ ID NO 3
<211> LENGTH: 21
<212> TYPE: DNA
<213> ORGANISM: Homo sapiens

<400> SEQUENCE: 3
ttctcactgt gtctctcctc c                                                 21

<210> SEQ ID NO 4
<211> LENGTH: 18
<212> TYPE: DNA
<213> ORGANISM: Homo sapiens

<400> SEQUENCE: 4
gtgggacagg ggcactca                                                     18

<210> SEQ ID NO 5
<211> LENGTH: 18
<212> TYPE: DNA
<213> ORGANISM: Homo sapiens

<400> SEQUENCE: 5
atcatggggc cctgagcc                                                     18

<210> SEQ ID NO 6
<211> LENGTH: 1341
<212> TYPE: DNA
<213> ORGANISM: Homo sapiens
<220> FEATURE:
<221> NAME/KEY: CDS
<222> LOCATION: (26)..(808)
<221> NAME/KEY: sig_peptide
<222> LOCATION: (26)..(97)
<221> NAME/KEY: sig_peptide
<222> LOCATION: (77)..(97)
<223> OTHER INFORMATION: pro-sequence
<221> NAME/KEY: mat_peptide
<222> LOCATION: (98)..(808)

<400> SEQUENCE: 6
cctggccgtg gacacctgtg tcagc atg tgg gac ctg gtt ctc tcc atc gcc         52
                            Met Trp Asp Leu Val Leu Ser Ile Ala
                                              -20 ttg tct gtg ggg tgc act ggt gcc gtg ccc ctc atc cag tct cgg att        100
Leu Ser Val Gly Cys Thr Gly Ala Val Pro Leu Ile Gln Ser Arg Ile
-15                 -10                 -5                -1  1

-continued

```
gtg gga ggc tgg gag tgt gag aag cat tcc caa ccc tgg cag gtg gct    148
Val Gly Gly Trp Glu Cys Glu Lys His Ser Gln Pro Trp Gln Val Ala
          5                  10                  15 gtg tac agt cat gga tgg gca cac tgt ggg ggt gtc ctg gtg cac ccc    196
Val Tyr Ser His Gly Trp Ala His Cys Gly Gly Val Leu Val His Pro
         20                  25                  30 cag tgg gtg ctc aca gct gcc cat tgc cta aag aag aat agc cag gtc    244
Gln Trp Val Leu Thr Ala Ala His Cys Leu Lys Lys Asn Ser Gln Val
 35                  40                  45 tgg ctg ggt cgg cac aac ctg ttt gag cct gaa gac aca ggc cag agg    292
Trp Leu Gly Arg His Asn Leu Phe Glu Pro Glu Asp Thr Gly Gln Arg
 50                  55                  60                  65 gtc cct gtc agc cac agc ttc cca cac ccg ctc tac aat atg agc ctt    340
Val Pro Val Ser His Ser Phe Pro His Pro Leu Tyr Asn Met Ser Leu
                 70                  75                  80 ctg aag cat caa agc ctt aga cca gat gaa gac tcc agc cat gac ctc    388
Leu Lys His Gln Ser Leu Arg Pro Asp Glu Asp Ser Ser His Asp Leu
             85                  90                  95 atg ctg ctc cgc ctg tca gag cct gcc aag atc aca gat gtt gtg aag    436
Met Leu Leu Arg Leu Ser Glu Pro Ala Lys Ile Thr Asp Val Val Lys
        100                 105                 110 gtc ctg ggc ctg ccc acc cag gag cca gca ctg ggg acc acc tgc tac    484
Val Leu Gly Leu Pro Thr Gln Glu Pro Ala Leu Gly Thr Thr Cys Tyr
115                 120                 125 gcc tca ggc tgg ggc agc atc gaa cca gag gag ttc ttg cgc ccc agg    532
Ala Ser Gly Trp Gly Ser Ile Glu Pro Glu Glu Phe Leu Arg Pro Arg
130                 135                 140                 145 agt ctt cag tgt gtg agc ctc cat ctc ctg tcc aat gac atg tgt gct    580
Ser Leu Gln Cys Val Ser Leu His Leu Leu Ser Asn Asp Met Cys Ala
                150                 155                 160 aga gct tac tct gag aag gtg aca gag ttc atg ttg tgt gct ggg ctc    628
Arg Ala Tyr Ser Glu Lys Val Thr Glu Phe Met Leu Cys Ala Gly Leu
            165                 170                 175 tgg aca ggt ggt aaa gac act tgt ggg ggt gat tct ggg ggt cca ctt    676
Trp Thr Gly Gly Lys Asp Thr Cys Gly Gly Asp Ser Gly Gly Pro Leu
        180                 185                 190 gtc tgt aat ggg gtg ctt caa ggt atc aca tca tgg ggc cct gag cca    724
Val Cys Asn Gly Val Leu Gln Gly Ile Thr Ser Trp Gly Pro Glu Pro
195                 200                 205 tgt gcc ctg cct gaa aag cct gct gtg tac acc aag gtg gtg cat tac    772
Cys Ala Leu Pro Glu Lys Pro Ala Val Tyr Thr Lys Val Val His Tyr
210                 215                 220                 225 cgg aag tgg atc aag gac acc atc gca gcc aac ccc tgagtgcccc         818
Arg Lys Trp Ile Lys Asp Thr Ile Ala Ala Asn Pro
                230                 235 tgtcccaccc ctacctctag taaatttaag tccacctcac gttctggcat cacttggcct   878
ttctggatgc tggacacctg aagcttggaa ctcacctggc cgaagctcga gcctcctgag   938
tcctactgac ctgtgctttc tggtgtggag tccagggctg ctaggaaaag gaatgggcag   998
acacaggtgt atgccaatgt ttctgaaatg ggtataattt cgtcctctcc ttcggaacac  1058
tggctgtctc tgaagacttc tcgctcagtt tcagtgagga cacacacaaa gacgtgggtg  1118 accatgtttgt ttgtggggtg cagagatggg aggggtgggg cccacctgga agagtggaca  1178
gtgacacaag gtggacactc tctacagatc actgaggata agctggagcc acaatgcatg  1238
aggcacacac acagcaagga tgacgctgta aacatagccc acgctgtcct gggggcactg  1298
ggaagcctag ataaggccgt gagcagaaag aagggagga tcc                     1341
```

```
<210> SEQ ID NO 7
<211> LENGTH: 261
<212> TYPE: PRT
<213> ORGANISM: Homo sapiens

<400> SEQUENCE: 7

Met Trp Asp Leu Val Leu Ser Ile Ala Leu Ser Val Gly Cys Thr Gly
            -20                 -15                 -10

Ala Val Pro Leu Ile Gln Ser Arg Ile Val Gly Gly Trp Glu Cys Glu
            -5                  -1  1                5

Lys His Ser Gln Pro Trp Gln Val Ala Val Tyr Ser His Gly Trp Ala
    10                  15                  20

His Cys Gly Gly Val Leu Val His Pro Gln Trp Val Leu Thr Ala Ala
25                  30                  35                  40

His Cys Leu Lys Lys Asn Ser Gln Val Trp Leu Gly Arg His Asn Leu
                45                  50                  55

Phe Glu Pro Glu Asp Thr Gly Gln Arg Val Pro Val Ser His Ser Phe
                60                  65                  70

Pro His Pro Leu Tyr Asn Met Ser Leu Leu Lys His Gln Ser Leu Arg
            75                  80                  85

Pro Asp Glu Asp Ser Ser His Asp Leu Met Leu Leu Arg Leu Ser Glu
            90                  95                  100

Pro Ala Lys Ile Thr Asp Val Val Lys Val Leu Gly Leu Pro Thr Gln
105                 110                 115                 120

Glu Pro Ala Leu Gly Thr Thr Cys Tyr Ala Ser Gly Trp Gly Ser Ile
                125                 130                 135

Glu Pro Glu Glu Phe Leu Arg Pro Arg Ser Leu Gln Cys Val Ser Leu
                140                 145                 150

His Leu Leu Ser Asn Asp Met Cys Ala Arg Ala Tyr Ser Glu Lys Val
                155                 160                 165

Thr Glu Phe Met Leu Cys Ala Gly Leu Trp Thr Gly Gly Lys Asp Thr
            170                 175                 180

Cys Gly Gly Asp Ser Gly Gly Pro Leu Val Cys Asn Gly Val Leu Gln
185                 190                 195                 200

Gly Ile Thr Ser Trp Gly Pro Glu Pro Cys Ala Leu Pro Glu Lys Pro
                205                 210                 215

Ala Val Tyr Thr Lys Val Val His Tyr Arg Lys Trp Ile Lys Asp Thr
            220                 225                 230

Ile Ala Ala Asn Pro
            235

<210> SEQ ID NO 8
<211> LENGTH: 1358
<212> TYPE: DNA
<213> ORGANISM: Homo sapiens
<220> FEATURE:
<221> NAME/KEY: CDS
<222> LOCATION: (43)..(825)
<221> NAME/KEY: sig_peptide
<222> LOCATION: (43)..(114)
<223> OTHER INFORMATION: prepro-sequence
<221> NAME/KEY: sig_peptide
<222> LOCATION: (94)..(114)
<223> OTHER INFORMATION: pro-sequence
<221> NAME/KEY: mat_peptide
<222> LOCATION: (115)..(825)

<400> SEQUENCE: 8
cctggccgtg gacacctcct ggccgtggac acctgtgtca gc atg tgg gac ctg      54
```

```
                                        Met Trp Asp Leu
gtt ctc tcc atc gcc ttg tct gtg ggg tgc act ggt gcc gtg ccc ctc    102
Val Leu Ser Ile Ala Leu Ser Val Gly Cys Thr Gly Ala Val Pro Leu
-20             -15                 -10                 -5 atc cag tct cgg att gtg gga ggc tgg gag tgt gag aag cat tcc caa    150
Ile Gln Ser Arg Ile Val Gly Gly Trp Glu Cys Glu Lys His Ser Gln
            -1  1               5                   10 ccc tgg cag gtg gct gtg tac agt cat gga tgg gca cac tgt ggg ggt    198
Pro Trp Gln Val Ala Val Tyr Ser His Gly Trp Ala His Cys Gly Gly
            15                  20                  25 gtc ctg gtg cac ccc cag tgg gtg ctc aca gct gcc cat tgc cta aag    246
Val Leu Val His Pro Gln Trp Val Leu Thr Ala Ala His Cys Leu Lys
            30                  35                  40 aag aat agc cag gtc tgg ctg ggt cgg cac aac ctg ttt gag cct gaa    294
Lys Asn Ser Gln Val Trp Leu Gly Arg His Asn Leu Phe Glu Pro Glu
45              50                  55                  60 gac aca ggc cag agg gtc cct gtc agc cac agc ttc cca cac ccg ctc    342
Asp Thr Gly Gln Arg Val Pro Val Ser His Ser Phe Pro His Pro Leu
            65                  70                  75 tac aat atg agc ctt ctg aag cat caa agc ctt aga cca gat gaa gac    390
Tyr Asn Met Ser Leu Leu Lys His Gln Ser Leu Arg Pro Asp Glu Asp
            80                  85                  90 tcc agc cat gac ctc atg ctg ctc cgc ctg tca gag cct gcc aag atc    438
Ser Ser His Asp Leu Met Leu Leu Arg Leu Ser Glu Pro Ala Lys Ile
            95                  100                 105 aca gat gtt gtg aag gtc ctg ggc ctg ccc acc cag gag cca gca ctg    486
Thr Asp Val Val Lys Val Leu Gly Leu Pro Thr Gln Glu Pro Ala Leu
            110                 115                 120 ggg acc acc tgc tac gcc tca ggc tgg ggc agc atc gaa cca gag gag    534
Gly Thr Thr Cys Tyr Ala Ser Gly Trp Gly Ser Ile Glu Pro Glu Glu
125             130                 135                 140 ttc ttg cgc ccc agg agt ctt cag tgt gtg agc ctc cat ctc ctg tcc    582
Phe Leu Arg Pro Arg Ser Leu Gln Cys Val Ser Leu His Leu Leu Ser
            145                 150                 155 aat gac atg tgt gct aga gct tac tct gag aag gtg aca gag ttc atg    630
Asn Asp Met Cys Ala Arg Ala Tyr Ser Glu Lys Val Thr Glu Phe Met
            160                 165                 170 ttg tgt gct ggg ctc tgg aca ggt ggt aaa gac act tgt ggg ggt gat    678
Leu Cys Ala Gly Leu Trp Thr Gly Gly Lys Asp Thr Cys Gly Gly Asp
            175                 180                 185 tct ggg ggt cca ctt gtc tgt aat ggg gtg ctt caa ggt atc aca tca    726
Ser Gly Gly Pro Leu Val Cys Asn Gly Val Leu Gln Gly Ile Thr Ser
            190                 195                 200 tgg ggc cct gag cca tgt gcc ctg cct gaa aag cct gct gtg tac acc    774
Trp Gly Pro Glu Pro Cys Ala Leu Pro Glu Lys Pro Ala Val Tyr Thr
205             210                 215                 220 aag gtg gtg cat tac tgg aag tgg atc aag gac acc atc gca gcc aac    822
Lys Val Val His Tyr Trp Lys Trp Ile Lys Asp Thr Ile Ala Ala Asn
            225                 230                 235 ccc tgagtgcccc tgtcccaccc ctacctctag taaatttaag tccacctcac        875
Pro gttctggcat cacttggcct ttctggatgc tggacacctg aagcttggaa ctcacctggc   935
cgaagctcga gcctcctgag tcctactgac ctgtgctttc tggtgtggag tccagggctg   995
ctaggaaaag gaatgggcag acacaggtgt atgccaatgt ttctgaaatg ggtataattt  1055
cgtcctctcc ttcggaacac tggctgtctc tgaagacttc tcgctcagtt tcagtgagga  1115
cacacacaaa gacgtgggtg accatgttgt ttgtggggtg cagagatggg aggggtgggg  1175
```

```
cccacctgga agagtggaca gtgacacaag gtggacactc tctacagatc actgaggata      1235
agctggagcc acaatgcatg aggcacacac acagcaagga tgacgctgta aacatagccc      1295
acgctgtcct gggggcactg ggaagcctag ataaggccgt gagcagaaag aagggagga      1355 tcc                                                                   1358
```

<210> SEQ ID NO 9
<211> LENGTH: 260
<212> TYPE: PRT
<213> ORGANISM: Homo sapiens

<400> SEQUENCE: 9

```
Met Trp Asp Leu Val Leu Ser Ile Ala Leu Ser Val Gly Cys Thr Gly
        -20                 -15                 -10

Ala Val Pro Leu Ile Gln Ser Arg Ile Val Gly Gly Trp Glu Cys Glu
         -5                 -1  1                   5

Lys His Ser Gln Pro Trp Gln Val Ala Val Trp Ser His Gly Trp Ala
 10                  15                  20                  25

His Cys Gly Gly Val Leu Val His Pro Gln Trp Val Leu Thr Ala Ala
                 30                  35                  40

His Cys Leu Lys Lys Asn Ser Gln Val Trp Leu Gly Arg His Asn Leu
             45                  50                  55

Phe Glu Pro Glu Asp Thr Gly Gln Arg Val Pro Val Ser His Ser Phe
         60                  65                  70

Pro His Pro Tyr Asn Met Ser Leu Leu Lys His Gln Ser Leu Arg Pro
     75                  80                  85

Asp Glu Asp Ser Ser His Asp Leu Met Leu Leu Arg Leu Ser Glu Pro
 90                  95                 100                 105

Ala Lys Ile Thr Asp Val Val Lys Val Leu Gly Leu Pro Thr Gln Glu
                110                 115                 120

Pro Ala Leu Gly Thr Thr Cys Tyr Ala Ser Gly Trp Gly Ser Ile Glu
            125                 130                 135

Pro Glu Glu Phe Leu Arg Pro Arg Ser Leu Gln Cys Val Ser Leu His
        140                 145                 150

Leu Leu Ser Asn Asp Met Cys Ala Arg Ala Tyr Ser Glu Lys Val Thr
    155                 160                 165

Glu Phe Met Leu Cys Ala Gly Leu Trp Thr Gly Gly Lys Asp Thr Cys
170                 175                 180                 185

Gly Gly Asp Ser Gly Gly Pro Leu Val Cys Asn Gly Val Leu Gln Gly
                190                 195                 200

Ile Thr Ser Trp Gly Pro Glu Pro Cys Ala Leu Pro Glu Lys Pro Ala
            205                 210                 215

Val Tyr Thr Lys Val Val His Tyr Trp Lys Trp Ile Lys Asp Thr Ile
        220                 225                 230

Ala Ala Asn Pro
    235
```

<210> SEQ ID NO 10
<211> LENGTH: 72
<212> TYPE: DNA
<213> ORGANISM: Homo sapiens
<220> FEATURE:
<221> NAME/KEY: misc_feature
<223> OTHER INFORMATION: nucleotide sequence encoding the prepro-
      sequence of the hK2 protein

<400> SEQUENCE: 10

-continued

```
atgtgggacc tggttctctc catcgccttg tctgtggggt gcactggtgc cgtgcccctc    60
atccagtctc gg                                                         72
```

<210> SEQ ID NO 11
<211> LENGTH: 24
<212> TYPE: PRT
<213> ORGANISM: Homo sapiens
<220> FEATURE:
<221> NAME/KEY: misc_feature
<223> OTHER INFORMATION: prepro-sequence of hK2 protein

<400> SEQUENCE: 11

```
Met Trp Asp Leu Val Leu Ser Ile Ala Leu Ser Val Gly Cys Thr Gly
1               5                   10                  15

Ala Val Pro Leu Ile Gln Ser Arg
            20
```

<210> SEQ ID NO 12
<211> LENGTH: 21
<212> TYPE: DNA
<213> ORGANISM: Homo sapiens
<220> FEATURE:
<221> NAME/KEY: misc_feature
<223> OTHER INFORMATION: nucleotide sequence encoding the pro-sequence
      of the hK2 protein

<400> SEQUENCE: 12

```
gtgcccctca tccagtctcg g                                               21
```

<210> SEQ ID NO 13
<211> LENGTH: 7
<212> TYPE: PRT
<213> ORGANISM: Homo sapiens
<220> FEATURE:
<221> NAME/KEY: misc_feature
<223> OTHER INFORMATION: pro-sequence of the hK2 protein

<400> SEQUENCE: 13

```
Val Pro Leu Ile Gln Ser Ala
1               5
```

<210> SEQ ID NO 14
<211> LENGTH: 17
<212> TYPE: PRT
<213> ORGANISM: Homo sapiens
<220> FEATURE:
<221> NAME/KEY: SIGNAL
<222> LOCATION: (1)..(17)
<223> OTHER INFORMATION: Signal peptide of the hK2 protein

<400> SEQUENCE: 14

```
Met Trp Asp Leu Val Leu Ser Ile Ala Leu Ser Val Gly Cys Thr Gly
1               5                   10                  15

Ala
```

HUMAN GLANDULAR KALLIKREIN-1 (HK2)

Figures 1A, 1B, 1C, 1D:
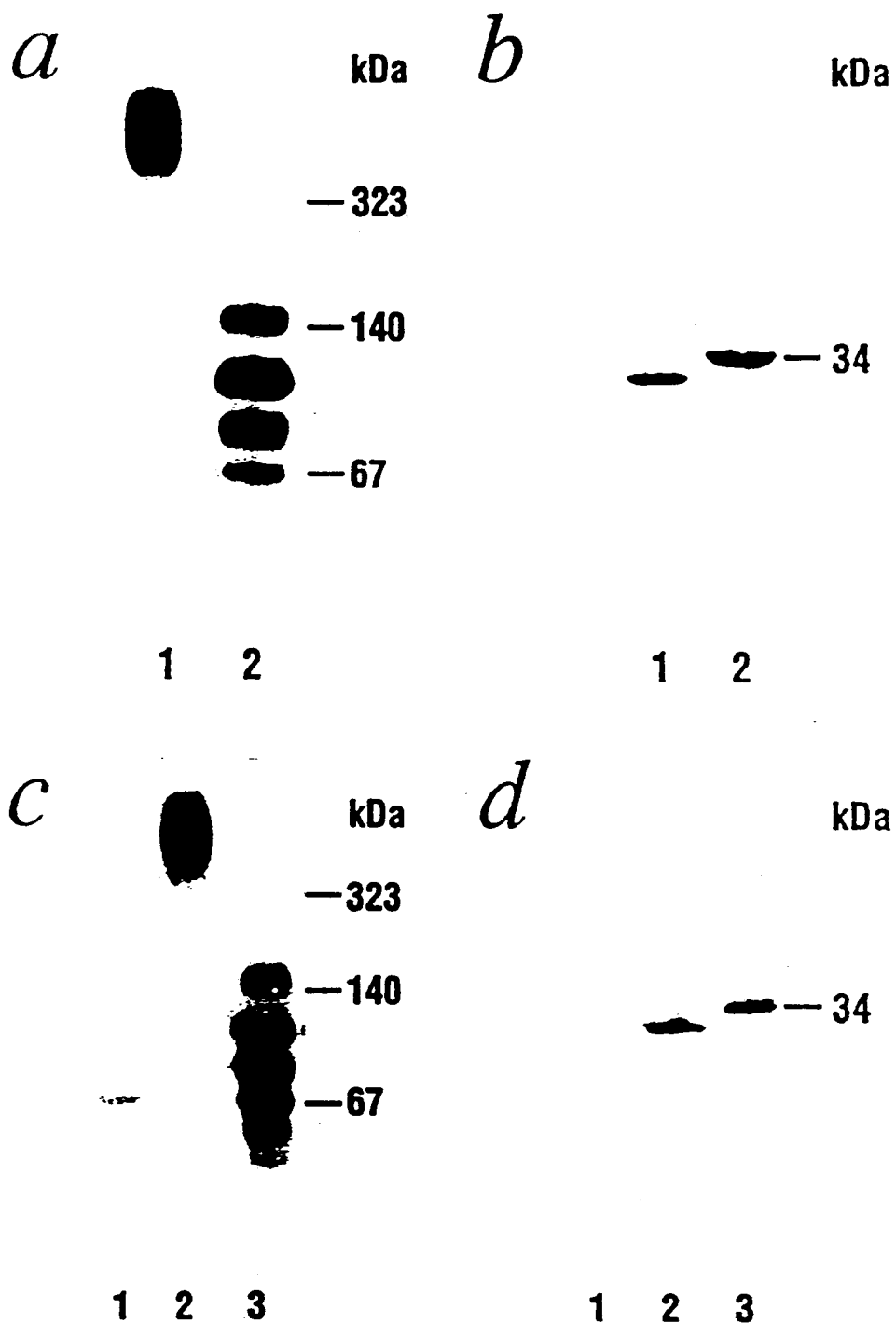

The present invention relates to novel proteins. In particular, it relates to a novel form of human glandular kallikrein-1 (hK2) encoded by a newly-identified hK2 gene and use of recombinant DNA techniques to obtain proteins encoded by the hK2 genes, including the mature protein encoded by the previously recognised hK2 gene, $Arg^{226}$-hK2, as an active protein.

The human glandular kallikrein gene family is composed of genes encoding three different proteins: prostate specific antigen (PSA), glandular kallikrein-1 (hK2) and pancreatic/renal kallikrein (KLK1). These genes are located on chromosome 19 and the PSA and hK2 genes are aligned at a distance of 12 kb(1). The similarity of the coding region of the human KLK1 gene to the coding regions of the human PSA and K2 genes is 74% and 75% respectively. The coding regions of the hPSA and hK2 genes are 85% homologous and the promoter regions of the same genes are 91% homologous. The KLK1 gene encodes the true kallikrein. KLK1 has a kininogenase activity and it is expressed in kidney, pancreas and salivary gland (2). By in situ hybridization, the hPSA and hK2 genes have been shown to be expressed only in prostatic epithelial cells. Despite the similarity of the hK2 and hPSA genes, the expression level of the hK2 gene at mRNA level is only about 10–30% ot that of the hPSA gene in the prostate (3). When tested with LNCaP cells, clear up-regulation of the mRNA levels for both hK2 and hPSA was observed in the presence of androgens (4).

Recently, further results have indicated that expression of hK2 and hPSA is not in fact prostate specific as previously believed. By Southern blot analysis with gene-specific oligonucleotide probes after RT-PCR, expression of all three previously identified human kallikrein genes has been detected in the human endometrium (5). hPSA has also been detected in milk of lactating women by immunoassay (6). It has additionally been found that 30–40% of breast tumours as well as steroid hormone stimulated normal breast tissue samples contain hPSA (7).

An hK2 gene has been isolated from a human genomic fetal liver DNA library and sequenced (8a). The nucleotide sequence (SEQ ID NO:6) of the five coding exons of this hK2 gene was found to encode a 261 amino acid preproprotein (SEQ ID NO:7) with a signal peptide of 17 amino acids (SEQ ID NO:14) and an activation peptide of 7 amino acids (SEQ ID NO:13) like PSA. hK2 has been found to possess the typical catalytic triad (His41-Asp96-Serl89) of serine proteases. The presence of an aspartate residue at amino acid position 183 in hK2 fits with a trypsin-like substrate activity for this protein. In PSA, there is a serine residue at the same position which accounts for PSA in contrast exhibiting chymotrypsin-like activity (8).

The function of PSA is the cleavage of semenogelin clots (9), but the function of hK2 is unknown. The concentration of PSA in serum is increased in cancer and hyperplasia of the prostate gland and PSA is widely used as a marker for the detection and monitoring of prostate cancer (10). Because of the high homology between the hPSA and hK2 genes, an hK2 protein has, however, remained to be purified. Also, the purity of PSA is not always unambiguous. This leads to problems with hPSA assays that are based on polyclonal or monoclonal antibodies raised against hPSA.

An hK2 protein has now been obtained free of hPSA contamination by cloning hK2 cDNA from a human prostate cancer tissue cDNA library in an expression vector and expressing the cDNA in appropriate host cells. More specifically, an hK2 protein has been produced by providing a baculovirus expression vector encoding a prepro-hK2 protein in insect cells (see Examples 4 and 5). While only use of a baculovirus expression vector system for production of an hK2 protein is described herein, in particular a recombinant Autographa California Nuclear Polyhedrosis virus (AcNPV) containing a coding sequence for prepro-hK2 under the control of the polyhedrin promoter, other expression vector systems commonly employed for production of human proteins may be employed. If, however, an expression vector encoding a prepro-hK2 protein is used, for example, to transform bacterial cells, e.g. E. coli cells, it will be appreciated that unlike in the case of the above baculovirus expression vector system, the pre-pro-sequence will not be removed by post-translational processing to give directly the corresponding mature protein, e.g. active mature $Arg^{226}$-hK2. By cloning an hK2 cDNA (SEQ ID NO: 8) from a human prostate cDNA library, an hK2 cDNA has now been identified which has one base difference from the coding sequence for hK2 previously reported. This difference at base position 790 (C to T) of SEQ ID NO: 8 equates with an amino acid change at amino acid position 226 of SEQ ID NO:9 from Arg to Trp. That this observed base difference was not an artifact of the cDNA cloning and sequencing procedure but reflects the existence of a previously unidentified hK2 gene was confirmed by using PCR to amplify the hK2 gene from genomic DNA of a number of human prostate and leucocyte samples (see Example 2).

In one aspect, the present invention thus provides a protein which is $Trp^{226}$-hK2 (SEQ ID NO:9) having a sequence identical to $Arg^{226}$-hK2 (SEQ ID NO:8) apart from change of $Arg^{226}$ to Trp or which is $Trp^{226}$-hK2 having an N- and/or C-terminal extension and which retains the ability to bind $Trp^{226}$-hK2 antibodies or hPSA antibodies, with the proviso that where said protein is a naturally-occurring protein it is substantially free of other proteins with which it is ordinarily associated.

Such proteins include, in addition to $Trp^{226}$-hK2 in substantially pure form, for example, $proTrp^{226}$-hK2 or prepro-$Trp^{226}$-hK2 in substantially pure form wherein $Trp^{226}$-hK2 is joined at the N-terminus to the pro- or prepro-sequences (SEQ ID NO:13 and SEQ ID NO:11, respectively) previously identified for $Arg^{226}$-hK2. A further novel protein forming an embodiment of the present invention is $Trp^{226}$-hK2 having the N-terminal dipeptide extension SerArg. It has been found that this derivative of $Trp^{226}$-hK2, rather than $Trp^{226}$-hK2 per se, is obtained by expression of a cDNA encoding prepro-$Trp^{226}$-hK2 in insect cells. It is detectable using a conventional hPSA immunoassay as commercially available for use in clinical studies thus demonstrating cross-reactivity with known anti-hPSA antibodies, but is inactive (see Example 3).

The present invention additionally extends to fragments of $Trp^{226}$-hK2 proteins as hereinbefore described which retain antigenicity and the $Trp^{226}$ amino acid residue. All such fragments and any protein having the $Trp^{226}$-hK2 sequence are included within the term $Trp^{226}$-hK2 protein used hereinafter.

In further aspects, the present invention provides an isolated DNA or recombinant DNA encoding a $Trp^{226}$-hK2 protein of the invention. Preferably, such a DNA may include the natural coding sequence for $Trp^{226}$-hK2, more preferably the complete natural coding sequence for prepro-$Trp^{226}$-hK2(SEQ ID NO:8). Such a recombinant DNA may be in the form of a vector, e.g. a plasmid or viral vector. Desirably, such a vector may be an expression vector which when present in host cells is capable of directing production of a $\text{Trp}^{226}$-hK2 protein of the invention in said cells or the culture medium. As hereinbefore indicated, particularly preferred, for example, is a baculovirus expression vector which when present in insect cells is capable of directing production of a $\text{Trp}^{226}$-hK2 protein of the invention in the culture medium or in said cells.

In additional aspects, the invention provides host cells containing a vector of the invention as hereinbefore described and a method of preparing a $\text{Trp}^{226}$-hK2 protein of the invention which comprises culturing host cells of the invention containing an expression vector under conditions whereby said protein is produced in the host cells or the culture medium and isolating said protein from said cells or medium. For example, where said cells are insect cells containing a baculovirus expression vector for expression in the cells of prepro-$\text{Trp}^{226}$-hK2, as hereinbefore indicated $\text{Trp}^{226}$-hK2 with the N-terminal dipeptide extension Ser-Arg may be purified from the culture medium. The purification protocol for this purpose may, for example, comprise a combination of ion-exchange chromatography and gel filtration chromatography steps (see Example 5). The $\text{Trp}^{226}$-hK2 derivative thus obtained may readily be subsequently converted to $\text{Trp}^{226}$-hK2 using techniques well known to those skilled in the art of protein engineering.

If in a baculovirus expression system as described above the prepro-$\text{Trp}^{226}$-hK2 sequence is substituted by a sequence encoding prepro-$\text{Arg}^{226}$-hK2 or $\text{Arg}^{226}$-hK2 joined to an alternative N-terminal sequence capable of processing in insect cells to give secreted mature $\text{Arg}^{226}$-hK2, active Arg226-hK2 may alternatively be isolated from the culture medium of host insect cells e.g. by a purification protocol comprising a combination of ion-exchange chromatography and gel filtration chromatography steps (see Example 5). Thus, there is also now additionally provided active $\text{Arg}^{226}$-hK2 substantially free of other proteins with which it is ordinarily associated and more particularly active $\text{Arg}^{226}$-hK2 in substantially pure form.

By active $\text{Arg}^{226}$-hK2 is meant a protein having the mature $\text{Arg}^{226}$-hK2 sequence and capable of hydrolyzing the synthetic chromogenic polypeptide substrate H-D-Pro-Phe-Arg-pNA. 2HCl, where pNA is paranitroaniline, in an assay procedure as described in Example 5. Active $\text{Arg}^{226}$-hK2 initially thus obtained may be subsequently digested to antigenic fragments. Isolation of $\text{Arg}^{226}$-hK2 or an antigenic fragment thereof may be followed by labelling of the protein.

For use, for example, in immunoassays, a protein of the present invention may be labelled with any label conventionally employed for labelling proteins. Thus, for example, a protein of the present invention may be labelled with a radiolabel, an enzyme label (e.g. alkaline phosphatase), a fluorescent label (e.g. fluorescein or rhodamine) a lanthanide or biotin (which may be detected by avidin or streptavidin conjugated to peroxidase).

It will be appreciated that a protein of the present invention may find use as a standard reference or to test for antibody reactivity to the protein in an appropriate immunoassay or immunohistochemical assay. Such tests may include, for example, testing for cross-reactivity to an antibody raised against hPSA, $\text{Arg}^{226}$-hK2 or $\text{Trp}^{226}$-hK2.

A protein of the present invention in unlabelled form may find use as an immunogen for the production of polyclonal or monoclonal antibodies. The protocol employed for polyclonal or monoclonal antibody production may conform with any of the conventional procedures known for antibody production. For this purpose, the protein will preferably be combined with an adjuvant, e.g. Freund's complete adjuvant, in an immunising composition. A suitable procedure for monoclonal antibody production to $\text{Trp}^{226}$-hK2 or $\text{Arg}^{226}$-hK2 may conform, for example, with the procedure described in Clinical Chemistry (1987) 33, 103–107 for obtaining monoclonal antibodies to human prostatic acid phosphatase or the procedure described in Clinical Chemistry (1990) 26, 92–95 for obtaining monoclonal antibodies to human prostate-specific antigen. An antibody so obtained may also be labelled in conventional manner, e.g. with a radioactive label, an enzyme label, a fluorescent label, a lanthanide or biotin.

By using $\text{Trp}^{226}$-hK2 as an immunogen for monoclonal antibody production and subsequently screening hybridomas using purified $\text{Trp}^{226}$-hK2 and commercially available purified hPSA, monoclonal antibodies can be selected which are capable of binding $\text{Trp}^{226}$-hK2, but not hPSA in human body samples and which are thus particularly valuable for diagnostic purposes. It will be appreciated that $\text{Arg}^{226}$-hK2, or a combination of $\text{Arg}^{226}$-hK2 and $\text{Trp}^{226}$-hK2, may alternatively be employed in such a procedure as the immunogen. Also, $\text{Arg}^{226}$-hK2 may be used in addition to, or instead of, $\text{Trp}^{226}$-hK2 in the screening protocol. Such an antibody screening protocol wherein both $\text{Arg}^{226}$-hK2 and $\text{Trp}^{226}$-hK2 are employed may be designed to select non-hPSA binding antibodies capable of distinguishing between $\text{Arg}^{226}$-hK2 and $\text{Trp}^{226}$-hK2.

Thus, in yet another aspect, the present invention provides an antibody, either in labelled or unlabelled form, capable of binding $\text{Trp}^{226}$-hK2 and/or Arg226-hK2, but not hPSA. The invention additionally provides hybridomas capable of producing such an antibody. By use of an antibody of the invention, Trp226-hK2 and/or $\text{Arg}^{226}$-hK2 may be specifically detected in a sample, e.g. a body sample. Such an antibody provides a new important tool for use in diagnosing prostatic disease.

The term "antibody" as used herein will be understood to include both complete antibody molecules and antigen-binding fragments thereof such as Fab and $F(ab')_2$ fragments. Humanised antibodies and fragments thereof are also included within the term "antibody".

It will be appreciated that in patients homozygous or heterozygous for the newly-identified $\text{Trp}^{226}$-hK2 gene, the $\text{Trp}^{226}$-hK2 protein sequence may serve as a marker for prostatic disease, e.g. for diagnosing cancer or hyperplasia of the prostate gland. Thus, in a still further aspect, the present invention provides a method of diagnosing prostatic disease in patients homozygous or heterozygous for the $\text{Trp}^{226}$-hK2 gene, which comprises determining whether there is altered expression or altered concentration of a protein encoded by said gene in prostate tissue or in human body fluids.

The following examples illustrate the invention with reference to FIGS. 1 and 2 as described below.

FIGS. 1a to 1d. Silver-stained polyacrylamide gel electrophoresis and immunoblot analysis of recombinant hK2 protein. The pure-recombinant $\text{Trp}^{226}$-hK2 protein (lane 1) and the commercial hPSA (lane 2) were silver-stained in native (1a) and reduced SDS-PAGE (1b). Rabbit polyclonal antibody raised against hPSA purified from seminal fluid was used to detect recombinant $\text{Arg}^{226}$-hK2 (lane 1), recombinant $\text{Trp}^{226}$-hK2 (lane 2 and commercial HPSA (lane 3) on blotted native PAGE (1c) and reduced SDS-PAGE (1d).

Figures 2A, 2B:
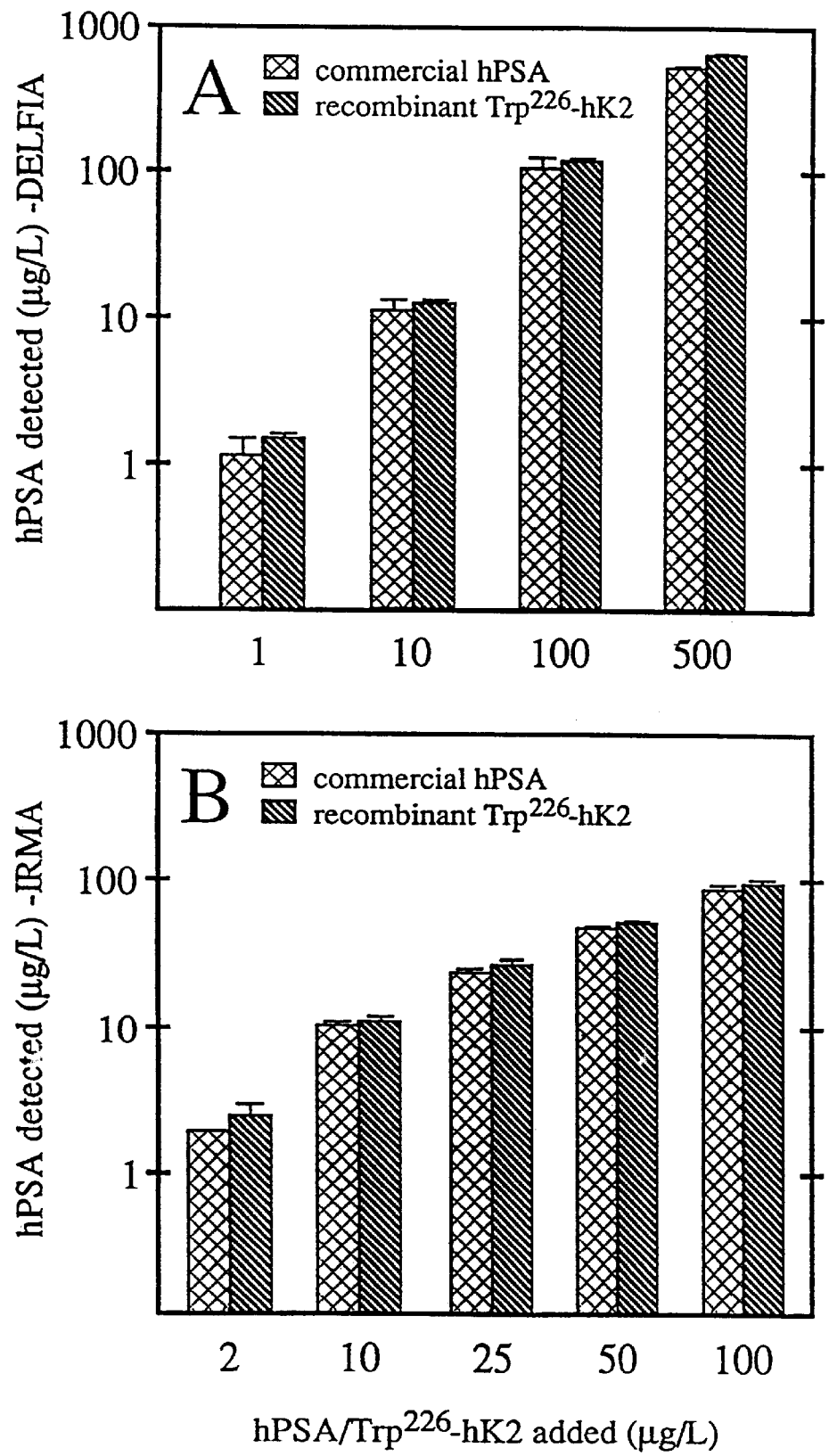

FIGS. 2A and 2B. Quantitative recoveries of recombinant $\text{Trp}^{226}$-hK2 and commercial hPSA by a time-resolved fluoroimmunoassay (1A) and IRMA (1B). Pure $\text{Trp}^{226}$-hK2 and commercial hPSA were diluted with the bovine serum albumin containing zero buffers of the kits to concentrations of 1, 10, 25, 50, 100 and 500 µl. These concentrations were assayed by the time-resolved fluoroimmunoassay and IRMA kits for hPSA. The data are means ±SD from three to five separate determinations.

EXAMPLE 1

Cloning of an hK2-cDNA from a Human Prostate Cancer Tissue cDNA Library

An hK2 cDNA was amplified from a human prostate cancer tissue cDNA library by PCR. For this PCR amplification, the N-terminal oligomer was (5'-TCCCCCGGGAGATCTCACCATGTGGGACCTGGTTCTC-3')(SEQ ID NO:1) and it contained SmaI and BglII restriction sites. The C-terminal oligomer was (5'-CGCTCTAGATCAGGGGTTGGCTGCGATGGT-3')(SEQ ID NO:2) and contained an XbaI restriction site in addition to the partial hK2 sequence. After confirmation of the hK2 sequence in the vector PCRII (Invitrogen) by the dideoxy method (Sanger et al. Proc. Natl. Acad. Sci USA (1977) 74, 5463), the prepro-hK2 cDNA was inserted into the BglII/XbaI site of the transfer vector pVL1392 (Invitrogen).

The coding sequence of this cDNA (SEQ ID NO:8) has a T at coding position 790. This differs from the human DNA coding sequence for hK2 (SEQ ID NO:6) previously reported by Schedlich et al. (8a) which has a C at the corresponding coding position.

EXAMPLE 2

Sequence Analysis of hK2 Genes in Human Prostate Tissue and Leukocyte Samples—Detections of the Arg226Trp-polymorphism Genomic DNA was isolated from human prostate tissue obtained by prostatectomy, biopsy or transurethral resection, and from human blood leukocytes. Female and young male blood leukocyte DNAs were used as control material. Specific oligonucleotides were used for PCR amplification and sequencing of the hK2 gene. For amplification, the N-terminal oligomer was 5'TTCTCACTGTGTCTCTCCTCC-3'(SEQ ID NO:3) and the biotin-labelled C-terminal oligomer was 5'GTGGGACAGGGGCACTCA-3'(SEQ ID NO:4). For PCR direct sequencing, the fluorescein amidite labelled oligomer was 5'ATCATGGGGCCCTGAGCC-3'(SEQ ID NO:5).

Variation was found at base position 790 (C to T) of SEQ ID NO:8. Sequenced DNA samples from both tissue and leukocyte specimens of 36 patients with prostatic diseases revealed that there occurs a polymorphism at this base position (Table 1a). In this limited specimen material, 13 out of 24 prostatic cancer patients were heterozygotes CT, 10 homozygotes CC and one homozygote TT. Eight of the 12 sequenced benign prostatic hyperplasia specimens were heterozygotes CT and four homozygotes CC. The same changes were detected in the tissue and leukocyte specimens. In the control material five female blood leukocyte DNA specimens out of 10 were heterozygotes CT, four homozygotes CC and one a homozygote TT, and in addition four young male blood leukocyte DNA specimens out of 6 were heterozygotes CT and two homozygotes CC. The frequency of $Arg^{226}$-allele was 69% among prostatic cancer patients (N=24), 67% among benign prostatic hyperplasia patients (N=12) and 66% among control material (N=16), and the frequency of $Trp^{226}$-allele was 31%, 33%, and 34%, respectively (Table 1b).

TABLE 1a

Genotypes as nucleotide position 792 in hK2.

| Specimen | CCa | CTb | TTc |
|---|---|---|---|
| Prostatic cancer (n = 24) | 10 | 13 | 1 |
| Benign prostatic hyperplasia (n = 12) | 4 | 8 | 0 |
| Female blood leukocyte (n = 10) | 4 | 5 | 1 |
| Young male blood leukocyte (n = 6) | 2 | 4 | 0 | aCC, homozygous Arg226-hK2; bCT, heterozygous; cTT, homoztgous Trp226-hK2

TABLE 1b

Frequency of the Arg226 and Trp226 alleles among prostatic cancer, benign prostatic hyperplasia and control blood leukocyte specimens.

| Allele | Prostatic cancer specimens (N = 24) | Benign prostatic hyperplasia specimens (N = 12) | Control blood leukocyte specimens (N = 16) |
|---|---|---|---|
| | no. (%) of alleles | | |
| Arg226 | 33 (69) | 16 (67) | 21 (66) |
| Trp226 | 15 (31) | 8 (33) | 11 (34) |

EXAMPLE 3

Quantitative Recovery of Recombinant $Trp^{226}$-hK2

The protein concentration of purified recombinant $Trp^{226}$-hK2 was estimated by the method of Lowry et al. (J. Biol. Chem. 1951; 193:265) with bovine serum albumin (Bio-Rad, Richmond, Calif.) as the standard. The recoveries of recombinant $Trp^{226}$-hK2 were further measured by time-resolved fluoroimmunoassay (DELFIA PSA kit, Wallac, Finland) and IRMA (Tandem®-R PSA kit, Hybritech Europe, Belgium). For the assay, the recombinant $Trp^{226}$-hK2 and commercial PSA were diluted with the "zero" standards of immunoassay kits containing bovine serum albumin.

The recoveries of $Trp^{226}$-hK2 and commercial hPSA tested in a fluoroimmunoassay detecting hPSA were 128±13% (mean±SD, n=20) and 107±20% (mean±SD, n=20), respectively, when compared to the calibrator of the fluoroimmunoassay kit. The recoveries when tested in an IRMA detecting hPSA were 110±14% (mean±SD, n=15) and 98±6% (mean±SD, n=15), respectively, when compared to the calibrator of the IRMA kit (FIG. 2).

The assays intended to measure serum hPSA concentrations were not specific to hPSA, but detected 100% of inactive hK2 added. The active recombinant hK2 was equally detectable in commercial fluoroimmunoassay and IRMA for hPSA.

EXAMPLE 4

Cloning of Prepro-hK2 cDNA in a Baculovirus Expression Vector and Expression in Insect Cells The same cloning procedure was employed as described in Vihko et al. Proc. Natl. Acad. Scl USA (1993) 90, 799–803 starting with co-transfection of AcNPV DNA (Invitrogen) and a PVL1392 transfer vector containing a prepro-hK2 cDNA obtained as in Example 1 into *Spodoptera frugiperda* (Sf9) cells (Invitrogen). The culture medium of insect cells containing recombinant AcNPV DNA was assayed for secreted protein capable of binding to hPSA monoclonal antibodies using an hPSA fluoroimmunoassay kit (DELFIA, Wallac).

Insect cells containing either a coding sequence for prepro-Trp$^{226}$-hK2 or prepro-Arg$^{226}$-hK2 were found to secrete into the culture medium protein capable of detection by the hPSA assay, although higher expression was observed with the prepro-Trp$^{226}$-hK2 coding sequence.

EXAMPLE 5

Purification of Recombinant Trp226-hK2 Protein and Active Arg$^{226}$hK2

The harvested medium from the recombinant virus infection was concentrated with a Pellicon cassette system (cutoff, 10 kDa, Millipore) and dialyzed into 5OmM sodium acetate buffer (pH 5.5). The concentrate was loaded onto a cation-exchange column (S-Sepharose HP 35/100, Pharmacia). After washing, the hK2 protein was eluted from the column with a linear salt gradient from 0.1 M to 0.25 M NaCl. Those fractions which were immunoreactive with polyclonal hPSA antibody (slot blot) were concentrated (Amicon) for gel filtration chromatography (Sephacryl S-75, Pharmacia) and eluted with 10 mM Tris-HCl at pH 7.0 containing 150 mM NaCl. The hK2 containing fractions were pooled and dialyzed in 20 mM sodium phosphate (pH 7.0) for cation exchange chromatography (Mono-S, Pharmacia). The hK2 protein was eluted from the column with a linear NaCl gradient (0–60 mM). The S-Sepharose and the Sephacryl S-75 columns were connected to BioPilot and the Mono-S column to an FPLC automated chromatography system (Pharmacia).

The purity of recombinant Trp$^{226}$-hK2 protein thus obtained was evaluated by SDS-PAGE, native PAGE and isoelectric focusing either by silver-staining or immunostaining (12). By reduced SDS-PAGE (FIGS. 1b, 1d), the molecular weight (Mr) of the recombinant Trp$^{226}$-hK2 protein was found to be approximately 33 kDa (12) while the Mr of commercial hPSA was found to be 34 kDa. When analysing the recombinant Trp$^{226}$-hK2 protein by ion spray mass spectrometry (ISMS), the detected average Mr was 27.4 kDa. In the case of silver-stained native PAGE (FIGS. 1a, 1c), the recombinant Trp$^{226}$-hK2 protein showed one band of 370 kDa while commercial hPSA showed four bands between 70 and 140 kDa. The heterogeneity seen with hPSA was possibly due to endoproteolytic cleavage of the protein into 2 or 4 polypeptide chains held together by disulphide bridges (13).

N-terminal amino acid analysis showed that posttranslational processing did not completely remove the preprosequence of prepro-Trp$^{226}$-hK2 in the insect cells.

Cleavage occurred between Gln-3 and Ser-2 rather than between Arg-1 and Ile-1. This form of recombinant hK2 was found to be inactive when assayed with synthetic polypeptides using the following assay procedure:

hK2 Hydrolysis Assay

Hydrolysis of H-D-Pro-Phe-Arg-pNA.2HCl and MeO-Suc-Arg-Pro-Tyr-pNA.HCl (Chromogenix AB) at a final concentration of 1 mM was measured at 405 nm. The reactions were performed at 370° C. and initiated by addition of the chromogenic substrate (50 ml) to 200 ml of 50 mM Tris buffer (pH 7.8) with 100 mM NaCl containing hK2 protein. After one hour, the reaction was stopped by adding 800 ml of 0.6 M acetic acid and the reaction rate (nmol pNA formed per ml) was calculated from a standard curve of pNA.

In serum, PSA predominately exists as a complex with α1-antichymotrypsin (15). Serine protease inhibitors like α1-antichymotrypsin and α1-antitrypsin usually react with the active site of the proteinase (16). It has been found, however, that recombinant Trp$^{226}$-hK2 protein obtained as above does not complex with either of these serpins.

The purification procedure given above may also be applied to recover Arg$^{226}$-hK2 from a culture medium. By this means, insect cells containing a prepro-Arg$^{226}$-hK2 coding sequence in an AcNPV vector operably-linked to a polyhedrin promoter have been shown to produce an active hK2 protein with trypsin-like activity. The immunostained native PAGE of the recovered Arg$^{226}$-hK2 protein showed a different pattern when compared to the recombinant Trp$^{226}$-hK2 protein (FIGS. 1b and 1c).

As hereinbefore indicated, purified recombinant hK2 proteins obtained by the above procedure and purified mature Trp$^{226}$-hK2, e.g. obtained by further processing of a Trp$^{226}$-hK2 derivative of the type discussed above, can be used as antigens for monoclonal antibody production. By using, for example, mature Trp$^{226}$-hK2 or mature Arg$^{226}$-hK2 for monoclonal antibody production in accordance with the procedure described by Höyhtyä et al in Clin. Chem. (1987) 33, 103–107 and screening hybridomas with one or both of Arg$^{226}$-hK2 and Trp$^{226}$-hK2 in addition to commercially available purified hPSA a monoclonal antibody can be obtained capable of distinguishing hK2 from hPSA in samples including human body samples, e.g. samples derived from human prostatic tissue. Such an antibody may be desirably labelled with Eu atoms as described in Vihko et al. Clinical Chemistry (1990) 26, 92–95.

REFERENCES

1. B. A. Evans et al., Blochem. 27, 3124 (1988). P. H. J. Riegman et al., FEBS Lett. 247, 123 (1989). P. H. J. Riegman et al., Genomics 14, 6 (1992).
2. A. R. Baker and J. Shine, DNA 4, 445 (1985). D. Fukushima et al., Biochemistry 24, 8037 (1985).
3. P. Chapdelaine et al., FEBS Lett 236, 205 (1988). S. -D. Qiu et al., J. Urol. 144, 1550 (1990). C. Y. -F. Young et al., Biochem 31, 818 (1992) L. Hakalahti et al., Int. J. Cancer 55, 1 (1993).
4. P. Henttu et al., Endocrinology 130, 766–772 (1992).
5. J. Elements and A. Mukhtar, Journal of Clinical Endocrinology and Metabolism 78, 1536 (1994).
6. H. Yu and E. P. Diamandis, Clin. Chem 41, 54 (1995).
7. H. Yu et al., Clin. Biochem. 27, 75 (1994).
8. (a) L. Schedlich et al., DNA 6, 429 (1987). (b) H. Neurath et al., Science 158, 1638, (1967) (c) J. Schaller et al., Eur. J. Biochem. 170, 111 (1987) (d) K. W. K. Watt et al., Proc. Natl. Acad. USA 83, 3166 (1986).
9. H. Lilia, J. Clin. Invest. 76, 1899 (1985).
10. T. A. Stamey et al., New Engl. J. Med. 317, 909 (1987).
11. P. Vihko et al., Proc. Natl. Acad. Sci USA 90, 799, (199R)
12. T. M. Jovin, Biochem. 12, 871 (1973). M. Wyckoff et al., Anal. Biochem, 78, 459 (1977). B. J. Davis, Ann. N.Y. Acad. Sci 121. 404 (1964). A. T. Andrews, in Electrophoresis, Theory, Techniques and Biochemical and Clinical Applications (A. R. Peacoce and W. F. Harrington eds.) Clarendon Press, Oxford, pp63–80 (1981). J. Heukeshoven and R. Dernick, Electrophoresis 6, 103 (1985). B. Prier and F. Russo-Marie, Anal. Biochem. 172, 338 (1988)
13. K. W. K. Watt et al., Proc. Natl. Acad. Sci USA 83, 3166 (1986).
14. H. Lilja et al., J. Biol. Chem. 24, 1894 (1989). A Christensson et al., Eur. J. Biochem. 194, 755 (1990)
15. A. Christensson et al., Eur. J. Biochem. 104, 755 (1990). H. Lilja et al., Clin. Chem. 37. 1618 (1991)
16. D. R. Boswell and R. Carrell, in Recent advances in clinical immunology, R. A. Thompson, ed. (Churchill Livingston, London, 1987) vol. 4, pp. 1–13.

What is claimed is:

1. An isolated Trp$^{226}$-hK2 polypeptide comprising an amino acid sequence of SEQ ID NO:9.

2. The polypeptide of claim 1, further comprising a N-terminal extension selected from the group consisting of a polypeptide having an amino acid sequence of SEQ ID NO:11, a polypeptide having an amino acid sequence of SEQ ID NO:13 and Ser-Arq.

3. The polypeptide of claim 2, wherein the N-terminal extension is Ser-Arg.

4. The polypeptide of claim 1, wherein said polypeptide is labeled.

5. A method of preparing a Trp$^{226}$-hK2 polypeptide, comprising:
    culturing host cells containing an expression vector comprising a polynucleotide sequence encoding a Trp$^{226}$-hK2 polypeptide of claim 1 under conditions whereby said polypeptide is produced in the host cells or the culture medium; and
    isolating said polypeptide from said cells or medium.

6. The method of claim 5, wherein the host cells are insect cells.

7. The method of claim 6, wherein the expression vector is a baculovirus expression vector.

8. The method of claim 6, wherein said vector comprises a polynucleotide sequence of SEQ ID NO:8 encoding prepro-Trp$^{226}$-hK2 and a promoter for insect cells, whereby a Trp$^{226}$-hK2 with a N-terminal dipeptide extension Ser-Arg is isolated from said cells or medium.

9. The method of claim 8, further comprising converting said Trp$^{226}$-hK2 with a N-terminal dipeptide extension Ser-Arg to said Trp$^{226}$-hK2 polypeptide.

10. The method of claim 5, wherein said isolation comprises ion-exchange chromatography or gel filtration chromatography.

11. A method of diagnosing a prostatic disease in a patient, comprising:

obtaining a sample of prostate tissue or body fluids from said patient; and determining whether there is altered expression or altered concentration of the protein of claim 1 in prostate tissue or in body fluids, whereby increased expression or concentration is an indication of having said prostatic disease.

12. The method of claim 11, wherein the polypeptide Trp$^{226}$-hK2 comprising the amino acid sequence SEQ ID NO:9 is used as a standard reference.

13. The method of claim 11, further comprising detecting Trp$^{226}$-hK2 using an antibody capable of binding Trp$^{226}$-hK2 but not hPSA.

14. A method of diagnosing a prostatic disease in a patient, comprising:

obtaining a sample of prostate tissue or body fluids from said patient; and determining whether there is altered expression or altered concentration of the protein of claim 2 in prostate tissue or in body fluids, whereby increased expression or concentration is an indication of having said prostatic disease.

15. The method of claim 14, wherein the polypeptide with SEQ ID NO:9 and further comprising an N-terminal extension selected from the group consisting of an amino acid sequence, SEQ ID NO:11, SEQ ID NO:13 and Ser-Arg, is used as a standard reference.

16. The method of claim 14, further comprising detecting Trp$^{226}$-hK2 using an antibody capable of binding Trp$^{226}$-hK2 but not hPSA.

17. A method for testing of an antibody reactivity to a polypeptide of claim 1 in an immunoassay or immunohistochemical assay comprising:

mixing together said antibody and said polypeptide; and testing reactivity between said antibody and said polypeptide.

18. A method for testing of an antibody reactivity to a polypeptide of claim 2 in an immunoassay or immunohistochemical assay comprising:

mixing together said antibody and said polypeptide; and testing reactivity between said antibody and said polypeptide.

* * * * *